(12) United States Patent
Hagopian et al.

(10) Patent No.: US 8,268,561 B2
(45) Date of Patent: Sep. 18, 2012

(54) METHODS FOR SCREENING FOR GENETIC PREDISPOSITION TO TYPE I DIABETES

(75) Inventors: William Hagopian, Seattle, WA (US); Hui Peng, Seattle, WA (US)

(73) Assignee: Pacific Northwest Research Institute, Seattle, WA (US)

( * ) Notice: Subject to any disclaimer, the term of this patent is extended or adjusted under 35 U.S.C. 154(b) by 350 days.

(21) Appl. No.: 12/420,722

(22) Filed: Apr. 8, 2009

(65) Prior Publication Data

US 2009/0311697 A1    Dec. 17, 2009

Related U.S. Application Data

(60) Provisional application No. 61/043,679, filed on Apr. 9, 2008.

(51) Int. Cl.
*C12Q 1/68* (2006.01)
*C12P 19/34* (2006.01)

(52) U.S. Cl. ...................... 435/6.11; 435/6.12

(58) Field of Classification Search .................. None
See application file for complete search history.

(56) References Cited

U.S. PATENT DOCUMENTS

| | | | |
|---|---|---|---|
| 5,039,606 | A | 8/1991 | Nepon |
| 5,541,065 | A | 7/1996 | Erlich et al. |
| 5,567,809 | A | 10/1996 | Apple et al. |
| 5,665,548 | A | 9/1997 | Erlich et al. |
| 6,534,272 | B2 | 3/2003 | Polychronakos et al. |
| 2004/0033516 | A1 | 2/2004 | Mougin |
| 2004/0126794 | A1 | 7/2004 | Bugawan et al. |
| 2008/0026378 | A1 | 1/2008 | Bottazzo et al. |

OTHER PUBLICATIONS

Nejentsev et al. (Diabetic Medicine, 1999, 16, 985-992).*
Wion et al. (Ann. N.Y. Acad. Sci. 1005: 400-403(2003).*
Hermann et al. (Tissue Antigens, 2003, 62: 162-169).*
Ahmedov et al. (Pediatric Diabetes 2006, 7:88-03).*
Bugawan et al. (Immunogenetics, 33:163-170, 1991).*
Bin-Cheng, Yin et al., "Construction of microarrays for genotyping of DQA using unmodified 45-mer oligonucleotide," Mol. Biotechnol., vol. 36, pp. 142-150 (2007).
Dunbar, Sherry A., "Applicaitons of Luminesx xMAP technology for rapid, high-throughput multiplexed nucleic acid detection," Clinica Chirnica Acta, vol. 363, pp. 71-82 (2006).
Ilonen. J. et al., "Genetic Screening for Type 1 Diabetes Risk in Finnish and Greet Populations—Stepwise Typing for Three Class II HLA Loci," Diabetes and Metabolism Research and Reviews, vol. 17, Suppl. 1, p. S25 (2001).
Lampasona, V. et al., "HLA-DQ screening for risk assessment of insulin dependent diabetes in northern Italy," Acta Dibetologica, Springer International, vol. 32, No. 3, pp. 137-142 (1995).
Redondo, Maria J. et al., "Specific Human Leukocyte Antigen DQ Influence on Expression of Antiislet Autoantibodies and Progression to Type 1 Diabetes," The Journal of Clinical Endocrinology & Metabolism, vol. 91, No. 5, pp. 1705-1713 (2006).
Buzzetti R. et al.,"Genetic prediction of type 1 diabetes in a population with low frequency of HLA risk genotypes and low incidence of the disease (the DIABFIN study)," Diabetes Metab Res Rev. vol. 20(2) pp. 137-143 (Jan. 2004).
Kukko, Marika MD et al., "Geographical variation in risk HLA-DQB1 genotypes for type 1 diabetes and signs of beta-cell autoimmunity in a high-incidence country," Diabetes Care, vol. 27(3) pp. 676-681 (Mar. 2004).
Cavan, D.A. et al., "Both DQA1 and DQB1 genes are implicated in HLA-associated protection from Type 1 (insulin dependent) diabetes mellitus in a British Caucasian population," Diabetologia, vol. 36, pp. 252-257 (1993).
Hermann, R. et al., "Genetic screening for individuals at high risk for type 1 diabetes in the general population using HLA Class II alleles as disease markers. A comparison between three European populations with variable rates of disease incidence," Diabetes/Metabolism Research and Reviews, vol. 20, pp. 322-329, (2004).
Khalil, Iman et al., "A Combination of HLA-DQbeta Asp57-Negative and HLA DQalpha Arg52 Confers Susceptibility to Insulin-dependent Diabetes Mellitus," J. Clin. Invest., vol. 85, pp. 1315-1319 (Apr. 1990).
Kiviniemi, Minna et al., "A High-Throughput Population Screening System for the Estimation of Genetic Risk for Type 1 Diabetes: An Application for the TEDDY (The Environmental Determinants of Diabetes in the Young) Study," Diabetes Technology & Therapeutics, vol. 9, No. 5, pp. 460-472 ( Nov. 5, 2007).
Emery, Lisa M. et al., "Newborn HLA-DR, DQ genotype screening: age- and ethnicity-specific type 1 diabetes risk estimates," Pediatr Diabetes, vol. 6(3) pp. 136-144 (Sep. 2005).
Itoh, Yoshiki et al., "High-throughput DNA typing of HLA-A,-B,-C, and DRB1 loci by a PCR-SSOP-Luminex method in the Japanese population," Immunogenetics, vol. 57, pp. 717-729 (2005).
Erlich, Henry et al., "HLA DR-DQ Haplotypes and Genotypes and Type 1 Diabetes Risk: Analysis of the Type 1 Diabetes Genetics Consortium Families," Diabetes Publish Ahead of Print, pp. 1-23 (Feb. 5, 2008).

* cited by examiner

*Primary Examiner* — Juliet Switzer

(74) *Attorney, Agent, or Firm* — Janet Sleath; Speckman Law Group PLLC

(57) ABSTRACT

A method of genetically screening large numbers of individuals to identify those individuals requiring follow-up testing for active Type I diabetes (T1D) is provided. The method includes obtaining a nucleic-acid containing biological sample from each individual and testing for the presence of specific combinations of HLA II alleles in the sample.

6 Claims, 3 Drawing Sheets

METHODS FOR SCREENING FOR GENETIC PREDISPOSITION TO TYPE I DIABETES

FIELD OF THE INVENTION

This application relates to methods for identifying individuals at risk of developing type I diabetes mellitus (T1D). More particularly, this application relates to methods for rapid, cost-effective, genetic screening of large numbers of individuals in order to identify those who should receive subsequent testing for active T1D.

BACKGROUND

Diabetes is a disorder characterized by persistent variable hyperglycemia due to either inadequate production of insulin by the body and/or an inadequate response by the body to insulin. Type I diabetes mellitus (T1D; also known as juvenile onset diabetes or insulin dependent diabetes) is an autoimmune disorder that typically develops in susceptible individuals during childhood, and involves progressive destruction of insulin-producing cells in the Islets of Langerhans of the pancreas. Patients with clinical T1D require regular insulin replacement therapy. Currently millions of people suffer from T1D with the overall incidence increasing at about 3-5% per year in most populations. While approximately 50% of the background risk of T1D is believed to be due to environmental factors, the remainder is due to genetic causes with up to 20 different genes influencing susceptibility to the disorder. Of the genetic influence, approximately 50% appears to involve genetic variations within the human leukocyte antigen (HLA) class II alleles HLA-DR and HLA-DQ.

Large-scale destruction of insulin-producing cells will already have taken place by the time clinical symptoms of T1D appear. The sub-clinical phase of the disease is characterized by the presence of auto-antibodies which target the individual's islet cells (ICAs), insulin (IAAs), glutamic acid decarboxylase (or GADAs) and/or tyrosine phosphatase (IA-2As).

Although there is currently no cure for T1D, early detection can reduce the likelihood of long-term complications, thereby both improving the quality of life and reducing costs resulting from repeated hospitalization. For example, it has been shown that children previously identified as being autoantibody-positive had a much lower hospitalization rate at the time of diagnosis (3.3% versus 44%), lower mean glycohemoglobin one month later, and lower mean insulin dose one year later. Predictive testing thus appears to lessen morbidity and medical costs at diagnosis and may lead to better metabolic function in the early period after diagnosis (1). Although no immunoprevention therapy has yet been identified that will delay or prevent disease, it is likely that such therapies will be more effective when implemented early, for example in the pre-clinical period before the autoimmune response is well advanced and the remaining islets are stressed.

Cases with a positive family history for T1D represent only 10-15% of newly diagnosed patients (2-5), therefore effective public health testing must test all children in order to identify pre diabetes. While the presence of islet autoantibodies is a sensitive and specific predictor of future T1D, autoantibodies appear at varying ages in different individuals, so periodic testing throughout childhood is necessary for prompt detection. Testing for autoantibodies is invasive and expensive, and thus a separate initial screening step is essential for overall cost-effectiveness. Since the peak incidence range for T1D is from about 4 to 15 years, predictive strategies must be applied early in life if they are to be informative.

The HLA-DR-DQ genetic locus is by far the most informative for T1D susceptibility and is estimated to account for approximately 50% of the genetic susceptibility to the disease (6). It has been suggested that HLA Class II genotyping might provide sufficient information for an initial screening step (6-8). Such genetic screening may be performed as early as the newborn period, well before disease onset. Initial HLA genetic screening can be used to identify susceptible children, who are then offered periodic autoantibody testing to detect activation of islet autoimmunity. This approach has been successfully demonstrated in large research studies, such as the Diabetes Auto-Immunity Study of the Young (DAISY) in Colorado (7), the Prospective Assessment of Newborns for Diabetes Autoimmunity (PANDA) in Florida (9), the Diabetes Prediction and Prevention (DIPP) study in Finland (10), and the Diabetes Evaluation in Washington (DEW-IT) study (11). The latter study further minimized cost and invasiveness by performing the HLA screening in coordination with a Washington State Dept. of Health Newborn Screening Program. These studies confirmed the ability of HLA screening to identify high-risk subjects for intervention or follow-up studies, but no consensus strategy for population-based T1D public health screening has emerged from them. Developing such a strategy is challenging because HLA haplotypes and genotypes form a continuum between highly susceptible and highly protective.

Kiviniemi et al. (12) describe a system for screening large numbers of individuals for genetic risk for T1D that employs multiple screening steps requiring large numbers of probes to identify different HLA alleles.

Assays employing DNA hybridization probes directed to a specific region of the HLA-DQβ region to detect a person's susceptibility to autoimmune diseases, such as T1D, are described in U.S. Pat. No. 5,665,548, with probes directed to the HLA-DR4 region and their use in diagnosing susceptibility to T1D being disclosed in U.S. Pat. No. 5,039,606. US Published Patent Application no. US2004/0126794 discloses methods for detecting increased or decreased risk for T1D by detecting the presence of specific HLA-C and/or HLA-A alleles. Methods for predicting autoimmune diabetes by detecting specific HLA Class II alleles are also described in U.S. Pat. No. 6,534,272. U.S. Pat. No. 5,567,809 describes specific primers and probes for HLA-DRβ DNA typing. US Published Patent Application no. US 2008/0026378 describes a method for predicting the onset of T1D comprising determining a subject's HLA genotype, assigning the subject's risk of developing T1D on the basis of the determined HLA genotype, measuring the concentration of at least one amino acid in a biological sample taken from the individual and combining the resulting information to predict the likelihood of onset of T1D.

While several methods for determining susceptibility to T1D using HLA DR-DQ have been described, such methods are high resolution and therefore not cost-effective for routine screening of large numbers of individuals. There thus remains a need in the art for materials and methods that may be effectively employed to screen populations for individuals at risk of developing T1D.

SUMMARY OF THE INVENTION

The present invention provides efficient, cost-effective and non-invasive methods for screening large numbers of individuals in order to identify individuals who are at risk of developing T1D and who should therefore receive follow-up testing for development of T1D, such as testing for the presence of autoantibodies indicative of pre-clinical T1D. Materials for use in such methods are also provided. The disclosed methods provide a practical means for screening large populations in order to implement public health strategies aimed at minimizing the occurrence and associated costs of clinical T1D. As described in detail below, the inventors have employed a simple algorithm to convert the risk of developing T1D due to the presence of specific HLA Class II haplotypes into genotype-based risk in order to maximize performance of a HLA DR-DQ screen.

The methods disclosed herein comprise obtaining a nucleic acid-containing (for example, DNA-containing) biological sample from an individual to be tested, and amplifying DNA in the sample using primers specific for exons 2 of the HLA DQB1, DQA1 and/or DRB1 loci. The amplified DNA is then used for identification of specific alleles by one of several well-known methods. For example, the amplified DNA can be contacted with combinations of oligonucleotide probes directed against specific alleles, in the method generally known as SSOP, or "sequence specific oligonucleotide probe". The presence or absence of binding between the probe(s) and the amplified DNA sample is indicative of the presence or absence of the specific allele(s). Alternatively, the amplified DNA can be sequenced directly, for example on an Applied Biosystems 310 genetic analyzer (Perkin Elmer Applied Biosystems, Foster City, Calif.) or similar equipment. A method employing selective primer extension can also be used to identify specific alleles. Finally, the initial DNA amplification can employ primers which, instead of amplifying exons 2 of all DQA1 and/or DQB1 alleles, are designed with even greater specificity to amplify only specific alleles, in the method known as "sequence specific primers". In this case, successful DNA amplification itself implies allele identity.

The specific DQA1 and/or DQB1 alleles which are identified by one of the above methods are then used to detect and/or infer haplotypes previously identified as being indicative of either resistance (R) or susceptibility (S) to T1D development, or as being neutral (N) with regards to T1D predisposition. In general, an individual is not recommended for follow-up autoantibody testing if the genetic screen indicates the presence of a resistant (R) haplotype and/or the absence of a susceptible (S) allele. However, the presence of a certain allele may "forgive", or negate, the presence of another specific allele. Specific combinations of alleles to be tested for, or probed, are discussed below and identified in Table 1 below. The combinations of alleles (and therefore the probes) are selected in order to maximize the number of future T1D cases included in autoantibody screening (i.e. maximize the sensitivity of the screening), while also minimizing the number of individuals recommended for follow-up autoantibody screening (i.e. maximizing the specificity).

The disclosed methods are homogeneous for all samples (i.e. all samples may be tested with the same combination(s) of probes), and allow determining of genotype at the minimum resolution needed to define high and low risk DR-DQ haplotypes in order to determine T1D genetic risk. Unlike prior art methods, individuals requiring follow-up testing for autoantibodies are identified using a simple method that can be readily employed for high-throughput screening of large numbers of individuals.

In specific embodiments, methods for identifying an individual in need of follow-up testing for T1D are provided, the methods comprising testing for the presence of a first HLA Class II allele, a second HLA Class II allele and a third HLA Class II allele in a nucleic acid sample obtained from the individual, wherein the first allele is DQB1*0301, the second allele is DQA1*020X, and the third allele is selected from the group consisting of: (a) DQB1*0602/0603; (b) DQB1*050X/060X; and (c) DQA1*01, where X=any integer. The presence of any one of the first, second and third alleles indicates that the individual is not in need of follow-up testing for T1D.

In one embodiment, the third allele is DQB1*050X/060X or DQA1*010X (where X=any integer) and the method further comprises testing for the presence of a fourth HLA Class II allele selected from the group consisting of: (i) DQB1*0604; and (ii) DQB1*0501, wherein the presence of the fourth allele negates the use of the third allele to indicate that the individual is not in need of follow-up testing for T1D.

In further embodiments, the methods additionally include testing for the presence of a fifth HLA Class II allele, wherein the fifth allele is DQB1*0503/0601, and wherein the presence of any one of the first, second, third and fifth alleles indicates that the individual is not in need of follow-up testing for T1D. The nucleic acid-containing sample may be further tested for the presence of a sixth HLA Class II allele, and/or for the presence of a seventh allele wherein the sixth allele is DQB1*0602/0603 and the seventh allele is DRB1*0403, and wherein the presence of any one of the first, second, third, fifth, sixth and seventh alleles indicates that the individual is not in need of follow-up testing for T1D.

In other embodiments, the methods further comprise testing for the presence of an eighth HLA Class II allele and a ninth HLA Class II allele, wherein the eighth allele is DQB1*0302 and the ninth allele is DQB1*020X (also referred to as DQB1*020X), and wherein the presence of any one of the first, second, third, fifth, sixth and seventh alleles or the absence of any one of the eighth and ninth alleles indicates that the individual is not in need of follow-up testing for T1D. In a related embodiment, the nucleic-acid containing sample may further be tested for the presence of a tenth HLA Class II allele, wherein the tenth allele is DQB1*040X (where X=any integer) and wherein the presence of the tenth allele negates the use of the ninth allele to indicate that the individual is in need of follow-up testing for T1D.

Materials for use in the disclosed methods, such as oligonucleotide probes that specifically hybridize, or bind, to the HLA Class II alleles of interest, are also provided. In one embodiment, kits are provided for identifying individuals at increased risk for developing T1D, such kits comprising combinations of oligonucleotide probes that are capable of hybridizing to the alleles of interest. The probes may already be labelled to facilitate detection of the presence or absence of binding between the probes and their targeted alleles, or the kits may include reagents for labelling the probes. The kits may also optionally include reagents to detect the label, and/or instructions for their use.

In yet a further embodiment, arrays, such as microarrays, are provided for use in the disclosed methods, such arrays comprising oligonucleotide probes that are capable of hybridizing to the specific combinations of alleles disclosed herein. The oligonucleotide probes may be immobilized on a substrate, such as a membrane or glass. Techniques and materials for preparing microarrays are well known in the art. Microarrays are available commercially and include those available from Affymetrix (Santa Clara, Calif.).

These and additional features of the present invention and the manner of obtaining them will become apparent, and the invention will be best understood, by reference to the following more detailed description and the accompanying drawings.

DETAILED DESCRIPTION

Figure 1:
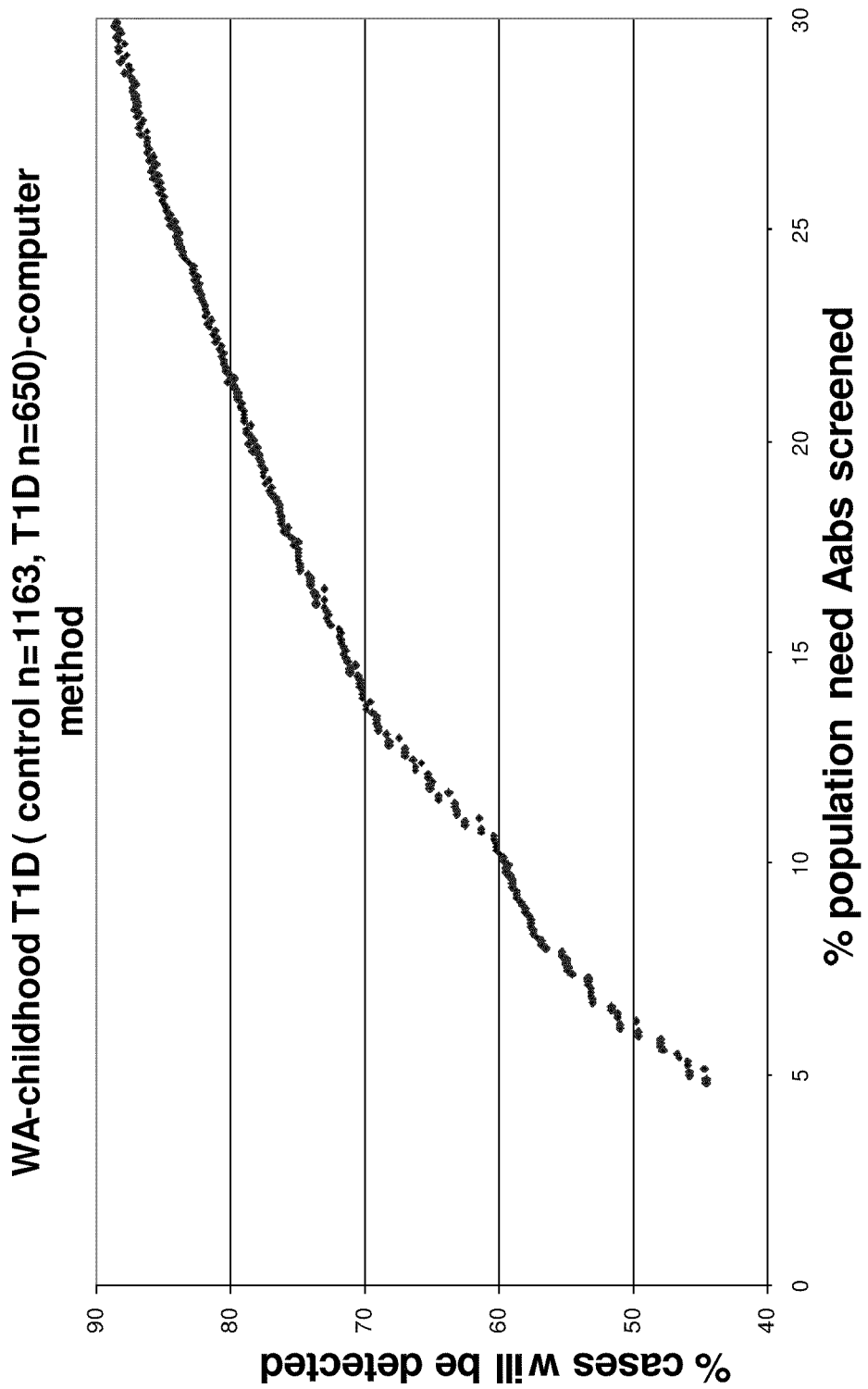
FIG. 1 shows the percentage of population needing autoantibody screening (specificity) versus percentage of T1D cases detected (sensitivity) for possible hypothetical risk strategies generated for the haplotypes shown in Table 2 using a computer program.

As outlined above, the present invention provides methods and materials for genetic screening of large populations to identify individuals who have increased genetic risk of developing T1D and should therefore receive follow-up screening for islet autoantibodies known to be indicative of the development of T1D. The methods include testing for the presence of HLA Class II haplotypes previously identified as being indicative of either resistance (R) or susceptibility (S) to T1D development, or as being neutral (N) with regards to T1D predisposition by contacting DNA obtained from the individuals with combinations of oligonucleotide probes that hybridize with specific S, N or R alleles.

As described in detail in Example 1 below, the inventors obtained extended HLA Class II DRB1-DQA1-DQB1 haplotype information for over 1000 individuals previously diagnosed to have T1D and over 1000 healthy control individuals. Based on this information, the haplotypes were ranked from those being most T1D resistant to those being most T1D susceptible. While the continuum of T1D risk in haplotypes ranges from highly susceptible to moderately susceptible to neutral to moderately resistant to highly resistant, the haplotype risk was assigned more concisely to three categories, namely susceptible (S), neutral (N) and resistant (R). Based on the known dominant protection of previously identified resistant haplotypes, a paradigm was developed to combine the haplotypes to provide two categories of genotypes, namely those associated with a high risk of developing T1D (S/S, S/N; i.e. individuals who should receive follow-up autoantibody screening), and those associated with a low risk of developing T1D (N/N, R/S, R/N, R/R; i.e. individuals to be excluded from follow-up autoantibody screening). Including "N" as a third haplotype risk level allowed for greater stratification, while reducing the genotype risk levels to two makes the autoantibody follow up practical. Intermediate, or moderate, risk classifications are not considered when determining whether or not an individual should receive follow-up screening.

Groups of alleles in the S, N and R categories were subsequently established for several different sensitivity/specificity strategies. In order to create a cost-effective method for detecting T1D cases in a large population of individuals, strategies were developed that minimized the number of individuals receiving autoantibody screening (i.e. maximized the specificity) while maximizing the number of future T1D cases detected (i.e. maximizing the sensitivity).

In these strategies, detection of various combinations of the following R alleles is used to identify the presence of the R haplotypes and therefore identify individuals who can rapidly be excluded from the group requiring follow-up autoantibody testing: DQB1*0301; DQA1*020X (also referred to as DQA1*02); DQB1*0602/0603; DQB1*050X/060X; DQB1*0602/0603; DQA1*010X; and DRB1*0403 (or DRB1*0403/0406/0407/0411), where X=any integer. Examples of specific strategies employing R alleles are shown in Tables 1A-C. Tables 1A-C include the total numbers of individuals tested in different populations (row 1) and the number of T1D cases captured in each population for each specific strategy, wherein WA Cau=number of healthy Caucasians tested; WA all race=total number of healthy subjects tested (regardless of race); all race, all DM=total number of T1D subjects tested; all race, T1D ons<22=total number of T1D subjects with an age at onset of less than 22 tested (regardless of race); Cau, all DM=number of Caucasian T1D subjects tested; and Cau, T1D ons<22=number of Caucasian T1D subjects with an age at onset of less than 22 tested.

TABLE 1A

| Strat. # | Resistant probes for elimination | Refine resistant info | Susceptible probe | Refine susceptible info |
|---|---|---|---|---|
| 1 | DQB1*0301 DQA1*02 DQB1*0602 DQB1*0603 | | | |
| 2 | DQB1*0301 DQA1*02 DQB1*0503 DQB1*0601 DQB1*0602 DQB1*0603 | | | |
| 3 | DQB1*0301 DQA1*02 DQB1*0503 DQB1*0601 DQB1*0602 DQB1*0603 DRB1*0403 | | | |
| 4 | DQB1*0301 DQA1*02 DQB1*05 DQB1*06 | | | |
| 5 | DQB1*0301 DQA1*02 DQB1*05 DQB1*06 | DQB1*0604 | | |
| 6 | DQB1*0301 DQA1*02 DQB1*05 DQB1*06 | DQB1*0501 | | |
| 7 | DQB1*0301 DQA1*02 DQB1*05 DQB1*06 | DQB1*0604 DQB1*0501 | | |
| 8 | DQB1*0301 DQA1*02 DQA1*01 | | | |
| 9 | DQB1*0301 DQA1*02 DQA1*01 | DQB1*0604 | | |
| 10 | DQB1*0301 DQA1*02 DQA1*01 | DQB1*0501 | | |
| 11 | DQB1*0301 DQA1*02 DQA1*01 | DQB1*0604 DQB1*0501 | | |
| 12 | DQB1*0301 DQA1*02 DQB1*05 DQB1*06 DRB1*0403 | | | |
| 13 | DQB1*0301 DQA1*02 DQB1*05 DQB1*06 DRB1*0403 | DQB1*0604 | | |
| 14 | DQB1*0301 DQA1*02 DQB1*05 DQB1*06 DRB1*0403 | DQB1*0501 | | |
| 15 | DQB1*0301 DQA1*02 DQB1*05 DQB1*06 DRB1*0403 | DQB1*0604 DQB1*0501 | | |
| 16 | DQB1*0301 DQA1*02 DQA1*01 DRB1*0403 | | | |
| 17 | DQB1*0301 DQA1*02 DQA1*01 DRB1*0403 | DQB1*0604 | | |
| 18 | DQB1*0301 DQA1*02 DQA1*01 DRB1*0403 | DQB1*0501 | | |
| 19 | DQB1*0301 DQA1*02 DQA1*01 DRB1*0403 | DQB1*0604 DQB1*0501 | | |
| 20 | DQB1*0301 DQA1*02 DQB1*0602 DQB1*0603 | | DQB1*0302 DQB1*02 | |
| 21 | DQB1*0301 DQA1*02 DQB1*0503 DQB1*0601 DQB1*0602 DQB1*0603 | | DQB1*0302 DQB1*02 | |
| 22 | DQB1*0301 DQA1*02 DQB1*0503 DQB1*0601 DQB1*0602 DQB1*0603 DRB1*0403 | | DQB1*0302 DQB1*02 | |
| 23 | DQB1*0301 DQA1*02 DQB1*05 DQB1*06 | | DQB1*0302 DQB1*02 | |
| 24 | DQB1*0301 DQA1*02 DQB1*05 DQB1*06 | DQB1*0604 | DQB1*0302 DQB1*02 | |

TABLE 1A-continued

| Strat. # | Resistant probes for elimination | Refine resistant info | Susceptible probe | Refine susceptible info |
|---|---|---|---|---|
| 25 | DQB1*0301 DQA1*02 DQB1*05 DQB1*06 | DQB1*0501 | DQB1*0302 DQB1*02 | |
| 26 | DQB1*0301 DQA1*02 DQB1*05 DQB1*06 | DQB1*0604 DQB1*0501 | DQB1*0302 DQB1*02 | |
| 27 | DQB1*0301 DQA1*02 DQA1*01 | | DQB1*0302 DQB1*02 | |
| 28 | DQB1*0301 DQA1*02 DQA1*01 | DQB1*0604 | DQB1*0302 DQB1*02 | |
| 29 | DQB1*0301 DQA1*02 DQA1*01 | DQB1*0501 | DQB1*0302 DQB1*02 | |
| 30 | DQB1*0301 DQA1*02 DQA1*01 | DQB1*0604 DQB1*0501 | DQB1*0302 DQB1*02 | |
| 31 | DQB1*0301 DQA1*02 DQB1*05 DQB1*06 DRB1*0403 | | DQB1*0302 DQB1*02 | |
| 32 | DQB1*0301 DQA1*02 DQB1*05 DQB1*06 DRB1*0403 | DQB1*0604 | DQB1*0302 DQB1*02 | |
| 33 | DQB1*0301 DQA1*02 DQB1*05 DQB1*06 DRB1*0403 | DQB1*0501 | DQB1*0302 DQB1*02 | |
| 34 | DQB1*0301 DQA1*02 DQB1*05 DQB1*06 DRB1*0403 | DQB1*0604 DQB1*0501 | DQB1*0302 DQB1*02 | |
| 35 | DQB1*0301 DQA1*02 DQA1*01 DRB1*0403 | | DQB1*0302 DQB1*02 | |
| 36 | DQB1*0301 DQA1*02 DQA1*01 DRB1*0403 | DQB1*0604 | DQB1*0302 DQB1*02 | |
| 37 | DQB1*0301 DQA1*02 DQA1*01 DRB1*0403 | DQB1*0501 | DQB1*0302 DQB1*02 | |
| 38 | DQB1*0301 DQA1*02 DQA1*01 DRB1*0403 | DQB1*0604 DQB1*0501 | DQB1*0302 DQB1*02 | |
| 39 | DQB1*0301 DQA1*02 DQB1*0602 DQB1*0603 | | DQB1*0302 DQB1*02 | DQB1*04 |
| 40 | DQB1*0301 DQA1*02 DQB1*0503 DQB1*0601 DQB1*0602 DQB1*0603 | | DQB1*0302 DQB1*02 | DQB1*04 |
| 41 | DQB1*0301 DQA1*02 DQB1*0503 DQB1*0601 DQB1*0602 DQB1*0603 DRB1*0403 | | DQB1*0302 DQB1*02 | DQB1*04 |
| 42 | DQB1*0301 DQA1*02 DQB1*05 DQB1*06 | | DQB1*0302 DQB1*02 | DQB1*04 |
| 43 | DQB1*0301 DQA1*02 DQB1*05 DQB1*06 | DQB1*0604 | DQB1*0302 DQB1*02 | DQB1*04 |
| 44 | DQB1*0301 DQA1*02 DQB1*05 DQB1*06 | DQB1*0501 | DQB1*0302 DQB1*02 | DQB1*04 |
| 45 | DQB1*0301 DQA1*02 DQB1*05 DQB1*06 | DQB1*0604 DQB1*0501 | DQB1*0302 DQB1*02 | DQB1*04 |
| 46 | DQB1*0301 DQA1*02 DQA1*01 | | DQB1*0302 DQB1*02 | DQB1*04 |
| 47 | DQB1*0301 DQA1*02 DQA1*01 | | DQB1*0302 DQB1*02 | DQB1*04 |
| 48 | DQB1*0301 DQA1*02 DQA1*01 | DQB1*0604 | DQB1*0302 DQB1*02 | DQB1*04 |
| 49 | DQB1*0301 DQA1*02 DQA1*01 | DQB1*0501 | DQB1*0302 DQB1*02 | DQB1*04 |
| 50 | DQB1*0301 DQA1*02 DQA1*01 | DQB1*0604 DQB1*0501 | DQB1*0302 DQB1*02 | DQB1*04 |
| 51 | DQB1*0301 DQA1*02 DQB1*05 DQB1*06 DRB1*0403 | | DQB1*0302 DQB1*02 | DQB1*04 |
| 52 | DQB1*0301 DQA1*02 DQB1*05 DQB1*06 DRB1*0403 | DQB1*0604 | DQB1*0302 DQB1*02 | DQB1*04 |
| 53 | DQB1*0301 DQA1*02 DQB1*05 DQB1*06 DRB1*0403 | DQB1*0501 | DQB1*0302 DQB1*02 | DQB1*04 |
| 54 | DQB1*0301 DQA1*02 DQB1*05 DQB1*06 DRB1*0403 | DQB1*0604 DQB1*0501 | DQB1*0302 DQB1*02 | DQB1*04 |
| 55 | DQB1*0301 DQA1*02 DQA1*01 DRB1*0403 | | DQB1*0302 DQB1*02 | DQB1*04 |
| 56 | DQB1*0301 DQA1*02 DQA1*01 DRB1*0403 | DQB1*0604 | DQB1*0302 DQB1*02 | DQB1*04 |
| 57 | DQB1*0301 DQA1*02 DQA1*01 DRB1*0403 | DQB1*0501 | DQB1*0302 DQB1*02 | DQB1*04 |
| 58 | DQB1*0301 DQA1*02 DQA1*01 DRB1*0403 | DQB1*0604 DQB1*0501 | DQB1*0302 DQB1*02 | DQB1*04 |

TABLE 1B

| Strat. # | WA Cau | WA all race | all race, all DM | all race, T1D ons < 22 | Cau, all DM | Cau, T1D ons < 22 | WA Cau | WA all race | all race, all DM | all race, T1D ons < 22 | Cau, all DM | Cau, T1D ons < 22 |
|---|---|---|---|---|---|---|---|---|---|---|---|---|
| | 972 | 1163 | 907 | 650 | 853 | 614 | 972 | 1163 | 907 | 650 | 853 | 614 |
| 1 | 224 | 296 | 653 | 486 | 613 | 458 | 23.0% | 25.5% | 72.0% | 74.8% | 71.9% | 74.6% |
| 2 | 196 | 248 | 647 | 484 | 610 | 456 | 20.2% | 213.0% | 71.3% | 74.5% | 71.5% | 74.3% |
| 3 | 183 | 226 | 635 | 475 | 598 | 447 | 18.8% | 19.4% | 70.0% | 73.1% | 70.1% | 72.8% |
| 4 | 76 | 98 | 450 | 346 | 431 | 331 | 7.8% | 8.4% | 49.6% | 53.2% | 50.5% | 53.9% |
| 5 | 94 | 116 | 506 | 382 | 483 | 364 | 9.7% | 10.0% | 55.8% | 58.8% | 56.6% | 59.3% |
| 6 | 144 | 181 | 562 | 429 | 537 | 409 | 14.8% | 15.6% | 62.0% | 66.0% | 63.0% | 66.6% |
| 7 | 162 | 199 | 618 | 465 | 589 | 442 | 16.7% | 17.1% | 68.1% | 71.5% | 69.1% | 72.0% |
| 8 | 76 | 98 | 450 | 346 | 431 | 331 | 7.8% | 8.4% | 49.6% | 53.2% | 50.5% | 53.9% |
| 9 | 94 | 116 | 506 | 382 | 483 | 364 | 9.7% | 10.0% | 55.8% | 58.8% | 56.6% | 59.3% |
| 10 | 144 | 181 | 562 | 429 | 537 | 409 | 14.8% | 15.6% | 62.0% | 66.0% | 63.0% | 66.6% |
| 11 | 162 | 199 | 618 | 465 | 589 | 442 | 16.7% | 17.1% | 68.1% | 71.5% | 69.1% | 72.0% |
| 12 | 70 | 85 | 440 | 338 | 421 | 323 | 7.2% | 7.3% | 48.5% | 52.0% | 49.4% | 52.6% |
| 13 | 86 | 101 | 495 | 373 | 472 | 355 | 8.8% | 8.7% | 54.6% | 57.4% | 55.3% | 57.8% |
| 14 | 133 | 162 | 551 | 421 | 526 | 401 | 13.7% | 13.9% | 60.7% | 64.8% | 61.7% | 65.3% |
| 15 | 149 | 178 | 606 | 456 | 577 | 433 | 15.3% | 15.3% | 66.8% | 70.2% | 67.6% | 70.5% |
| 16 | 70 | 85 | 440 | 338 | 421 | 323 | 7.2% | 7.3% | 48.5% | 52.0% | 49.4% | 52.6% |
| 17 | 86 | 101 | 495 | 373 | 472 | 355 | 8.8% | 8.7% | 54.6% | 57.4% | 55.3% | 57.8% |
| 18 | 133 | 162 | 551 | 421 | 526 | 401 | 13.7% | 13.9% | 60.7% | 64.8% | 61.7% | 65.3% |
| 19 | 149 | 178 | 606 | 456 | 577 | 433 | 15.3% | 15.3% | 66.8% | 70.2% | 67.6% | 70.5% |
| 20 | 172 | 212 | 621 | 468 | 596 | 448 | 17.7% | 18.2% | 68.5% | 72.0% | 69.9% | 73.0% |
| 21 | 157 | 191 | 619 | 466 | 594 | 446 | 16.2% | 16.4% | 68.2% | 71.7% | 69.6% | 72.6% |
| 22 | 144 | 169 | 607 | 457 | 582 | 437 | 14.8% | 14.5% | 66.9% | 70.3% | 68.2% | 71.2% |
| 23 | 74 | 93 | 445 | 342 | 429 | 329 | 7.6% | 8.0% | 49.1% | 52.6% | 50.3% | 53.6% |
| 24 | 89 | 108 | 499 | 377 | 479 | 361 | 9.2% | 9.3% | 55.0% | 58.0% | 56.2% | 58.8% |
| 25 | 131 | 160 | 550 | 421 | 530 | 404 | 13.5% | 13.8% | 60.6% | 64.8% | 62.1% | 65.8% |
| 26 | 146 | 175 | 604 | 456 | 580 | 436 | 15.0% | 15.0% | 66.6% | 70.2% | 68.0% | 71.0% |
| 27 | 74 | 93 | 445 | 342 | 429 | 329 | 7.6% | 8.0% | 49.1% | 52.6% | 50.3% | 53.6% |
| 28 | 89 | 108 | 499 | 377 | 479 | 361 | 9.2% | 9.3% | 55.0% | 58.0% | 56.2% | 58.8% |
| 29 | 131 | 160 | 550 | 421 | 530 | 404 | 13.5% | 13.8% | 60.6% | 64.8% | 62.1% | 65.8% |

TABLE 1B-continued

| Strat. # | WA Cau | WA all race | all race, all DM | all race, T1D ons < 22 | Cau, all DM | Cau, T1D ons < 22 | WA Cau | WA all race | all race, all DM | all race, T1D ons < 22 | Cau, all DM | Cau, T1D ons < 22 |
|---|---|---|---|---|---|---|---|---|---|---|---|---|
| 30 | 146 | 175 | 604 | 456 | 580 | 436 | 15.0% | 15.0% | 66.6% | 70.2% | 68.0% | 71.0% |
| 31 | 68 | 80 | 435 | 334 | 419 | 321 | 7.0% | 6.9% | 48.0% | 51.4% | 49.1% | 52.3% |
| 32 | 81 | 93 | 488 | 368 | 468 | 352 | 8.3% | 8.0% | 53.8% | 56.6% | 54.9% | 57.3% |
| 33 | 120 | 141 | 539 | 413 | 519 | 396 | 12.3% | 12.1% | 59.4% | 63.5% | 60.8% | 64.5% |
| 34 | 133 | 154 | 592 | 447 | 568 | 427 | 13.7% | 13.2% | 65.3% | 68.8% | 66.6% | 69.5% |
| 35 | 68 | 80 | 435 | 334 | 419 | 321 | 7.0% | 6.9% | 48.0% | 51.4% | 49.1% | 52.3% |
| 36 | 81 | 93 | 488 | 368 | 468 | 352 | 8.3% | 8.0% | 53.8% | 56.6% | 54.9% | 57.3% |
| 37 | 120 | 141 | 539 | 413 | 519 | 396 | 12.3% | 12.1% | 59.4% | 63.5% | 60.8% | 64.5% |
| 38 | 133 | 154 | 592 | 447 | 568 | 427 | 13.7% | 13.2% | 65.3% | 68.8% | 66.6% | 69.5% |
| 39 | 164 | 201 | 609 | 458 | 585 | 439 | 16.9% | 17.3% | 67.1% | 70.5% | 68.6% | 71.5% |
| 40 | 149 | 180 | 607 | 458 | 583 | 437 | 15.3% | 15.5% | 66.9% | 70.2% | 68.3% | 71.2% |
| 41 | 136 | 156 | 595 | 447 | 571 | 428 | 14.0% | 13.6% | 65.6% | 68.8% | 66.9% | 69.7% |
| 42 | 82 | 66 | 433 | 332 | 418 | 320 | 8.4% | 5.7% | 47.7% | 51.1% | 49.0% | 52.1% |
| 43 | 81 | 97 | 487 | 367 | 468 | 352 | 8.3% | 8.3% | 53.7% | 56.5% | 54.9% | 57.3% |
| 44 | 123 | 149 | 538 | 411 | 519 | 395 | 12.7% | 12.8% | 59.3% | 63.2% | 60.8% | 64.3% |
| 45 | 138 | 164 | 592 | 446 | 569 | 427 | 14.2% | 14.1% | 65.3% | 68.6% | 66.7% | 69.5% |
| 46 | 82 | 66 | 433 | 332 | 418 | 320 | 8.4% | 5.7% | 47.7% | 51.1% | 49.0% | 52.1% |
| 47 | 84 | 66 | 435 | 334 | 419 | 321 | 8.6% | 5.7% | 48.0% | 51.4% | 49.1% | 52.3% |
| 48 | 81 | 97 | 487 | 367 | 468 | 352 | 8.3% | 8.3% | 53.7% | 56.5% | 54.9% | 57.3% |
| 49 | 123 | 149 | 538 | 411 | 519 | 395 | 12.7% | 12.8% | 59.3% | 63.2% | 60.8% | 64.3% |
| 50 | 138 | 164 | 592 | 446 | 569 | 427 | 14.2% | 14.1% | 65.3% | 68.6% | 66.7% | 69.5% |
| 51 | 70 | 84 | 439 | 337 | 420 | 322 | 7.2% | 7.2% | 48.4% | 51.8% | 49.2% | 52.4% |
| 52 | 73 | 82 | 476 | 358 | 457 | 343 | 7.5% | 7.1% | 52.5% | 55.1% | 53.6% | 55.9% |
| 53 | 112 | 130 | 527 | 403 | 506 | 387 | 11.5% | 11.2% | 58.1% | 62.0% | 59.6% | 63.0% |
| 54 | 125 | 143 | 580 | 437 | 557 | 418 | 12.9% | 12.3% | 63.9% | 67.2% | 65.3% | 68.1% |
| 55 | 70 | 84 | 439 | 337 | 420 | 322 | 7.2% | 7.2% | 48.4% | 51.8% | 49.2% | 52.4% |
| 56 | 73 | 82 | 476 | 358 | 457 | 343 | 7.5% | 7.1% | 52.5% | 55.1% | 53.6% | 55.9% |
| 57 | 112 | 130 | 527 | 403 | 508 | 387 | 11.5% | 11.2% | 58.1% | 62.0% | 59.6% | 63.0% |
| 58 | 125 | 143 | 580 | 437 | 557 | 418 | 12.9% | 12.3% | 63.9% | 67.2% | 65.3% | 68.1% |

TABLE 1C

| Strat. # | |
|---|---|
| 1 | eliminate if any resistant probe pos |
| 2 | eliminate if any resistant probe pos |
| 3 | eliminate if any resistant probe pos |
| 4 | eliminate if any resistant probe pos |
| 5 | eliminate if has any resistant probe (but B0604 forgives B05/06 or A01) |
| 6 | eliminate if has any resistant probe (but B0501 forgives B05/06 or A01) |
| 7 | eliminate if has any resistant probe (but B0501 or B0604 forgives B05/06 or A01) |
| 8 | eliminate if any resistant probe pos |
| 9 | eliminate if has any resistant probe (but B0604 forgives B05/06 or A01) |
| 10 | eliminate if has any resistant probe (but B0501 forgives B05/06 or A01) |
| 11 | eliminate if has any resistant probe (but B0501 or B0604 forgives B05/06 or A01) |
| 12 | eliminate if any resistant probe pos |
| 13 | eliminate if has any resistant probe (but B0604 forgives B05/06 or A01) |
| 14 | eliminate if has any resistant probe (but B0501 forgives B05/06 or A01) |
| 15 | eliminate if has any resistant probe (but B0501 or B0604 forgives B05/06 or A01) |
| 16 | eliminate if any resistant probe pos |
| 17 | eliminate if has any resistant probe (but B0604 forgives B05/06 or A01) |
| 18 | eliminate if has any resistant probe (but B0501 forgives B05/06 or A01) |
| 19 | eliminate if has any resistant probe (but B0501 or B0604 forgives B05/06 or A01) |
| 20 | eliminate if has any resistant probe or if does not have susceptible probe |
| 21 | eliminate if has any resistant probe or if does not have susceptible probe |
| 22 | eliminate if has any resistant probe or if does not have susceptible probe |
| 23 | eliminate if has any resistant probe or if does not have susceptible probe |
| 24 | eliminate if has any resistant probe or if does not have susceptible probe (but B0604 forgives B05/06 or A01) |
| 25 | eliminate if has any resistant probe or if does not have susceptible probe (but B0501 forgives B05/06 or A01) |
| 26 | eliminate if has any resistant probe or if does not have susceptible probe (but B0501 or B0604 forgives B05/06 or A01) |
| 27 | eliminate if has any resistant probe or if does not have susceptible probe |
| 28 | eliminate if has any resistant probe or if does not have susceptible probe (but B0604 forgives B05/06 or A01) |
| 29 | eliminate if has any resistant probe or if does not have susceptible probe (but B0501 forgives B05/06 or A01) |
| 30 | eliminate if has any resistant probe or if does not have susceptible probe (but B0501 or B0604 forgives B05/06 or A01) |
| 31 | eliminate if has any resistant probe or if does not have susceptible probe |
| 32 | eliminate if has any resistant probe or if does not have susceptible probe (but B0604 forgives B05/06 or A01) |
| 33 | eliminate if has any resistant probe or if does not have susceptible probe (but B0501 forgives B05/06 or A01) |
| 34 | eliminate if has any resistant probe or if does not have susceptible probe (but B0501 or B0604 forgives B05/06 or A01) |
| 35 | eliminate if has any resistant probe or if does not have susceptible probe |
| 36 | eliminate if has any resistant probe or if does not have susceptible probe (but B0604 forgives B05/06 or A01) |
| 37 | eliminate if has any resistant probe or if does not have susceptible probe (but B0501 forgives B05/06 or A01) |
| 38 | eliminate if has any resistant probe or if does not have susceptible probe (but B0501 or B0604 forgives B05/06 or A01) |

TABLE 1C-continued

| Strat. # | |
|---|---|
| 39 | eliminate if has any resistant probe or if does not have susceptible probe (but DQB1*04 eliminates DQB1*02) |
| 40 | eliminate if has any resistant probe or if does not have susceptible probe (but DQB1*04 eliminates DQB1*02) |
| 41 | eliminate if has any resistant probe or if does not have susceptible probe (but DQB1*04 eliminates DQB1*02) |
| 42 | eliminate if has any resistant probe or if does not have susceptible probe (but DQB1*04 eliminates DQB1*02) |
| 43 | eliminate if has any resistant probe or if does not have susceptible probe (but B0604 forgives B05/06 or A01) (but DQB1*04 eliminates DQB1*02) |
| 44 | eliminate if has any resistant probe or if does not have susceptible probe (but B0501 forgives B05/06 or A01) (but DQB1*04 eliminates DQB1*02) |
| 45 | eliminate if has any resistant probe or if does not have susceptible probe (but B0501 or B0604 forgives B05/06 or A01) (but DQB1*04 eliminates DQB1*02) |
| 46 | eliminate if has any resistant probe or if does not have susceptible probe (but DQB1*04 eliminates DQB1*02) |
| 47 | eliminate if has any resistant probe or if does not have susceptible probe (but DQA1*04 eliminates DQB1*0201) |
| 48 | eliminate if has any resistant probe or if does not have susceptible probe (but B0604 forgives B05/06 or A01) (but DQB1*04 eliminates DQB1*02) |
| 49 | eliminate if has any resistant probe or if does not have susceptible probe (but B0501 forgives B05/06 or A01) (but DQB1*04 eliminates DQB1*02) |
| 50 | eliminate if has any resistant probe or if does not have susceptible probe (but B0501 or B0604 forgives B05/06 or A01) (but DQB1*04 eliminates DQB1*02) |
| 51 | eliminate if has any resistant probe or if does not have susceptible probe |
| 52 | eliminate if has any resistant probe or if does not have susceptible probe (but B0604 forgives B05/06 or A01) (but DQB1*04 eliminates DQB1*02) |
| 53 | eliminate if has any resistant probe or if does not have susceptible probe (but B0501 forgives B05/06 or A01) (but DQB1*04 eliminates DQB1*02) |
| 54 | eliminate if has any resistant probe or if does not have susceptible probe (but B0501 or B0604 forgives B05/06 or A01) (but DQB1*04 eliminates DQB1*02) |
| 55 | eliminate if has any resistant probe or if does not have susceptible probe |
| 56 | eliminate if has any resistant probe or if does not have susceptible probe (but B0604 forgives B05/06 or A01) (but DQB1*04 eliminates DQB1*02) |
| 57 | eliminate if has any resistant probe or if does not have susceptible probe (but B0501 forgives B05/06 or A01) (but DQB1*04 eliminates DQB1*02) |
| 58 | eliminate if has any resistant probe or if does not have susceptible probe (but B0501 or B0604 forgives B05/06 or A01) (but DQB1*04 eliminates DQB1*02) |

Detection of the following S alleles is used to identify the presence of S haplotypes, and therefore identify individuals who should be included in the group requiring follow-up autoantibody testing: DQB1*0302 and DQB1*020X (also referred to as DQB1*02). However, it should be noted that DQB1*020X is only useful when a probe for DQA1*020X is included in the test as the presence of DQA1*020X disqualifies DQB1*020X as representing a susceptible haplotype. Similarly, in those cases where DRB1*0403 is probed, its presence disqualifies DQB1*0302 as representing a susceptible haplotype. R alleles can be grouped in several ways for use with S alleles as shown in Table 1.

Other N alleles, such as DQB1*0501 and DQB1*0604, can be added to relieve elimination by DQB1*050X/060X or by DQA1*010X (the latter two are equivalent entities), as shown in Table 1. In addition, the allele DQB1*040X can be added to eliminate individuals who test positive for the S allele DQB1*020X.

The sensitivity and specificity of the screening method vary depending on the combination of alleles tested for. For example, testing only for the R alleles DQB1*0503/0601, DQB1*0301/0304, DQA1*020X results in a specificity of 28% and a sensitivity of 74.8%, while testing for the R alleles DQB1*0503/0601, DQB1*0301/0304, DQA1*020X, B0602/0603, and the S alleles DQB1*0302/0304 and DQB1*020X results in a specificity of 16% and a sensitivity of 71.7%. Testing for the R alleles DQB1*050X/060X, DQB1*0301/0304, DQA1*020X, and for the S alleles DQB1*0302/0304 and DQB1*020X, as well as for the S allele modifier DQB1*040X, yields a specificity of 5.7% and a sensitivity of 51.1%, as does testing for R alleles DQB1*0301/0304, DQA1*020X and DQA1*01 and S alleles DQB1*0302/0304 and DQB1*020X and S allele modifier DQB1*040X.

Cost effectiveness of the overall prediction strategy (HLA screening and autoantibody follow-up) is a key factor in design considerations and is greatly affected by the stringency (sensitivity, specificity) of the HLA screening step. The cost per T1D case identified is higher when a higher number of follow-up autoantibody tests need to be performed. It is known that performing initial genetic screening to determine which individuals should receive autoantibody screening provides significant cost-savings compared to autoantibody screening alone. Defining genotype risk through converting haplotype information helped to identify the majority of future T1D cases while minimizing the proportion of the population needing autoantibody follow up by maximizing performance of HLA DR-DQ in a T1D genetic screening role, thereby increasing sensitivity while maintaining specificity compared to strategies that employ simply the alleles or haplotypes previously identified. The impact of the improvement in the sensitivity on cost savings over a longer term will be sizeable, as it is known that children who participate in prospective follow-up autoantibody testing are less often hospitalized and have milder metabolic abnormalities at diagnosis. In a large population, some deaths and permanent morbidity are likely to be prevented by early diagnosis.

In order to identify the presence or absence of specific alleles in an individual, a nucleic acid (DNA and/or RNA) containing biological sample is first obtained from the individual. The biological sample may be, for example, blood, urine, saliva or sera. DNA and/or RNA may also be obtained from hair, skin, nails or other body tissue. The nucleic acid-containing sample is then subjected to polymerase chain reaction (PCR) to amplify exon 2 of the HLA DQA1 and DQB1 genes. Primers and techniques for use in PCR are well known to those in the art and include, but are not limited to, those described below in Example 1.

The presence of alleles of interest can be detected using methods known in the art, including, but not limited to, contacting the amplified nucleic acid-containing sample with one or more oligonucleotide probes that hybridize under stringent hybridization conditions to one or more polymorphisms associated with the alleles and detecting the hybridized, or bound, oligonucleotide probes. Oligonucleotide probes that may be effectively employed to detect the HLA II alleles of interest are well known in the art and include, for example, those described in U.S. Pat. No. 5,567,809, US Patent Publication no. 2004/0126794, Kiviniemi et al. Diabetes Technology & Therapeutics, 9:460-472 (2007)), and Itoh et al. Immunogenetics 57:717-729 (2005), the disclosures of which are hereby incorporated by reference.

Such oligonucleotide probes and primers are substantially complementary to one or more polymorphisms associated with the allele of interest. Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions.

As employed herein the term "stringent hybridization conditions" includes salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. In one specific example, "stringent hybridization conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In certain embodiments, sequence-specific oligonucleotide probes (SSOP; i.e. probes that hybridize specifically to the allele of interest) are immobilized on a solid substrate, such as a nylon membrane, using methods well known to those of skill in the art. The bound SSOP are contacted with the PCR-amplified nucleic acid sample for a period of time sufficient for the SSOP to hybridize to the target allele(s). The substrate is then washed to remove unhybridized sample and the presence of the bound SSOP is detected using methods known to those of skill in the art. For example, the oligonucleotide probes may be labelled with a moiety that allows detection of probe by spectroscopic methods. In one method, the nucleic acid-containing sample is amplified using biotinylated primers and the bound biotinylated PCR product is detected using streptavidin-horseradish peroxidase.

In an alternative embodiment, the presence or absence of specific alleles of interest is detected using a Delfia™ system (Perkin Elmer, Boston, Mass.), in which up to three different SSOPs, each labelled with a different detection reagent such as europium (Eu), terbium (Tb) or samarium (Sm), are simultaneously contacted with an amplified DNA sample. Binding of alleles to the labeled probes may then be detected using time-resolved fluorometry. For example, Sjoroos et al. (13) described a method for detecting two T1D susceptibility (*0201, *0302) and two T1D protective (*0301, *0602/0603) alleles of the HLA-DQB1 gene employing DNA amplification with PCR followed by simultaneous, allele-specific triple-label hybridization performed in microtitration wells using the Delfia™ system. Use of this type of system offers significant advantages, in that it enables simultaneous testing for the presence or absence of multiple alleles of interest.

Other techniques that may be effectively employed to detect hybridization between SSOP and alleles of interest include SSOP-Luminex™ methods as described by Itoh et al. (15). Such methods employ a flow cytometry dual-laser system to quantitatively detect fluorescently labelled oligonucleotides attached to color-coded microbeads and have previously been employed in high-throughput, high-resolution genotyping studies.

SSOP may also be employed in a high-throughput ELISA technique to detect the presence of alleles of interest. Such techniques are well known in the art and include, for example, those described in (16).

A plurality of oligonucleotide probes may be provided in a kit form. Such kits generally comprise multiple oligonucleotide probes, with each probe being specific for an allele of interest. In one embodiment useful for high-throughput assays, the oligonucleotide probe kits disclosed herein comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, 6,586,168, 6,284,460, 6,268,152, 6,156,501, 6,045,996, the disclosures of which are hereby incorporated by reference.

Oligonucleotide probes for use in the disclosed methods may be constructed synthetically using techniques well known in the art (See, for example, Gait, ed., *Oligonucleotide synthesis a practical approach*, IRL Press: Oxford, England, 1984). Automated equipment for the synthesis of oligonucleotides is available commercially from such companies as Perkin Elmer/Applied Biosystems Division (Foster City, Calif.) and may be operated according to the manufacturer's instructions. Alternatively, the probes may be constructed directly on the surface of an array using techniques taught, for example, in PCT Publication No. WO 95/00530.

Those of skill in the art will appreciate that alternative methods, such as restriction-fragment length polymorphism (RFLP), may also be employed to detect the presence or absence of specific alleles, or combinations of alleles, of interest in nucleic acid-containing biological samples. An additional method to determine the alleles present is to directly sequence the amplified exons 2 of DRB1, DQA1 and/or DQB1 using di-deoxy labeling followed by analysis on the Applied Biosystems 310 Genetic Analyzer or similar apparatus. Alternatively, a method employing selective primer extension can be used to identify specific alleles (14-16)

Another method that may be employed to detect specific alleles, is for the initial DNA amplification to employ primers which, instead of amplifying exons 2 of all DQA1 and/or DQB1 alleles, are designed with even greater specificity to amplify only specific alleles, in the method known as "sequence specific primers". In this case, successful DNA amplification itself implies allele identity.

The following examples are offered by way of illustration and not by way of limitation.

EXAMPLE 1

A large case-control cohort from Washington State was HLA-DQ genotyped to determine: a) what are the best strategies for population-wide HLA Class II screening in a typical U.S. population, and b) whether the best such strategy is sufficiently predictive to be useful in screening for a subsequent autoantibody testing program for cost-effective, public health-based preclinical T1D prediction as a prelude to risk counseling and ultimately to delay or prevent the onset of disease.

The most useful haplotype algorithms for maximum performance of HLA DR-DQ in a T1D genetic screening role were identified as described below. Medium-resolution inferred HLA DQA1-DQB1 haplotypes from 907 T1D cases and 1163 healthy subjects from Washington State were combined into genotypes to test all risk assessment strategies based on relative risk groupings (susceptible, neutral, resistant) of the individual haplotypes. DQB1*0302 haplotypes were further stratified by DRB1*040X subtypes before analysis. Computerized simulations tested all risk strategies representing all possible haplotype risk assignment combinations. Results were interpreted in light of desirable general pediatric T1D risk screening goals, namely sufficient sensitivity to include most future cases among subjects screening positive, and sufficient specificity to minimize the overall number who must undergo subsequent follow-up. Strategies with the highest combined sensitivity/specificity (% of future cases within % of pediatric population) were 51.1% within 6.8%, 65.1% within 12.1%, 72.5% within 15.1%, and 76.0% within 18.0%. There was slightly less sensitivity if adult onset, as well as childhood-onset, T1D cases were considered, and slightly greater sensitivity if only Caucasians were included.

Subjects—The unrelated healthy control cohort consisted of 1163 randomly selected subjects from a 4505-subject Washington State general population study (17) and a similar Washington State general population diabetes screening study, and excluded subjects with diabetes, those who were first degree relatives of current diabetes patients, and those with persistent islet autoantibodies. Type 1 diabetes subjects were recruited, consented and sampled from hospital wards or clinics, or specialty medical practices in Washington State. Blood was drawn for serum autoantibody testing and genomic DNA testing. Of 1094 consented and sampled diabetes cases (median diabetes duration 11.2 years), 1062 had sufficient DNA sampled for genotyping. For 72 cases, a serum C-peptide measurement was available. Inclusion criteria for childhood T1D (onset age<22 years), was positivity for any of the 3 islet autoantibodies OR random C-peptide<0.8 (18) OR first degree relative with autoantibody-confirmed T1D OR all of the following (BMI<25, no T2D first degree relatives, AND on continuous insulin therapy since diagnosis). Inclusion criteria for adult T1D (onset age 22 years or older) was positive T1D autoantibodies OR random C-peptide<0.8 OR a first degree relative with autoantibody-confirmed T1D. After application of the above inclusion criteria, a total of 907 cases (650 childhood T1D cases and 257 adult T1D cases) were included in the analysis. For all T1D cases, 93.3% were Non-Hispanic White, 0.8% Hispanic White, 1.5% Black, 1.1% Asian, and 3.3% other/undetermined. For healthy controls, 78.3% were Non-Hispanic White, 5.2% Hispanic White, 2.7% Black, 7.3% Asian and 6.4% other/undetermined.

Autoantibodies—Serum autoantibodies to the human diabetes islet autoantigens GAD65, the full cytoplasmic domain of IA2, and insulin were measured using separate radiobinding assays as described by Woo et al. (19).

Sequence-Based DQ Genotyping—Genotyping of HLA DQA1 and DQB1 utilized direct sequencing of amplified exon 2 of each gene using a Perkin Elmer/Applied Biosystems Inc. 310 automated sequencer. PCR templates consisted of either ⅛" dried bloodspots fixed in MeOH as described (11) or genomic DNA purified from whole frozen blood (QiaAmp, Qiagen). PCR primers for DQB1 exon 2 were GH29 and DB130 (20) and for DQA1 exon 2 were DQAAMP-A and DQAAMP-B (21). Allele frequencies and frequency of homozygosity were similar to those found in 1102 subjects combined from two large Washington State bone marrow transplant registries (22) and in published 11th International HLA Workshop data on North American Caucasians, Blacks and Japanese (23). This indicates that all DQA1 and DQB1 alleles were well amplified by our methods.

DRB1*04 subtyping—Subjects with DQ haplotypes expected to have DRB1*04 were further examined by low-resolution DR4 subtyping using Restriction Fragment Length Polymorphism (24). Published DRB1*04-specific PCR primers AB54 (sense) and AB60 (antisense) (20) were used to generate 257 bp amplicons for digestion with SacII and visualization by agarose gel electrophoresis. Cleavage to 199 bp and 58 bp fragments indicated common T1D-susceptible DR4 alleles (DRB1*0401/0402/0404/0405) while no cleavage indicated DR4 alleles generally conferring T1D resistance (DRB1*0403/406/407/411).

Algorithm—After identifying allele sequences for each gene, DQA1-DQB1 haplotypes were inferred based on published frequencies in Caucasians (25) and from the HLA 1991 workshop for Asian-Americans and Black Americans (23). Haplotypes were assigned into one of three categories, namely resistant (R), neutral (N) and susceptible (S), and each pair of haplotypes was then combined into an individual genotype. Based on the known dominance of resistant over susceptible haplotypes (26; 27), as well as the necessity of having at least one susceptible haplotype to be at risk of disease (28; 29), the genotypes R/S, R/N, R/R, and N/N were assigned to the low risk cohort, while S/S and S/N were assigned to the high risk cohort for which follow-up autoantibody testing was recommended.

Modest simplification of the haplotype list was done to allow each listing to contain sufficient numbers of subjects. Where practical typing refinements existed (e.g. DR4 subtyping), these were included to better resolve the haplotypes. In the case of ambiguous assignments, the most frequent DQA1-DQB1 combinations were chosen, which in all cases were at least 50-fold more prevalent overall than the non-chosen combinations. The list of haplotypes was then further simplified in three ways. First, in a limited number of cases, haplotypes identical at DQB1 but with minor differences at the fourth digit of DQA1 (e.g. 0102 and 0103) were grouped, provided that the grouped haplotypes did not differ substantially in relative disease risk based on published data (23). Second, DQA1*03 haplotypes with DQB1*0302 or 0304 were grouped together since these DQB1 alleles are structurally similar and do not differ substantially in relative disease risk. This grouping was particularly important since these grouped DQA1*030X-DQB1*0302/4 haplotypes were then divided into three groups based on DR4 subtyping (DRB1*0403 group, not DRB1*0403, and not DRB1*040X). Finally, four rare haplotypes (DQA1*030X-DQB1*0402, DQA1*0501-DQB1*0302/4, DQA1*0102-DQB1*0504 and DQA1*0101-DQB1*0608) which were each observed at a frequency of less than 1 in 500, were combined as "rare haplotypes" which included a total of 18 haplotype counts out of 4140 total haplotype counts.

The final result totaled 22 haplotypes or haplotype categories. Their frequencies among cases and controls, odds ratios (OR), and significance of association to T1D, are shown in Tables 2A and 2B. Tables 2A and 2B list these haplotypes in order from those which confer the greatest resistance to T1D (at the top of the tables), to those which confer the greatest susceptibility to T1D (at the bottom of the tables).

TABLE 2A

| | | All T1D | | | <22 T1D | | | |
|---|---|---|---|---|---|---|---|---|
| | frequency (n = 1788) n (%) | WA - all T1D (n = 1814) n (%) | Odds Ratio (95% CI) | p value (a = 0.0023) | WA - <22 T1D (n = 1300) n (%) | Odds Ratio (95% CI) | p value (a = 0.0023) | S = Susceptible N = Neutral R = Resistant |

Whole Washington State Population

| Haplotype | frequency (n = 1788) n (%) | WA - all T1D (n = 1814) n (%) | Odds Ratio (95% CI) | p value (a = 0.0023) | WA - <22 T1D (n = 1300) n (%) | Odds Ratio (95% CI) | p value (a = 0.0023) | S/N/R |
|---|---|---|---|---|---|---|---|---|
| 0103/4-0503 | 54 (3.02) | 2 (0.11) | 0.04 (0.01-0.16) | <0.0001 | 1 (0.08) | 0.02 (0.01-0.17) | <0.0001 | R |
| 0102/3/4-0602 | 242 (13.53) | 14 (0.77) | 0.05 (0.03-0.09) | <0.0001 | 6 (0.46) | 0.03 (0.01-0.07) | <0.0001 | R |
| 0601-0301 | 11 (0.62) | 1 (0.06) | 0.09 (0.02-0.70) | 0.0035 | 1 (0.08) | 0.12 (0.03-0.98) | 0.0176 | R |
| 0201-0303 | 62 (3.47) | 10 (0.55) | 0.15 (0.08-0.31) | <0.0001 | 5 (0.38) | 0.11 (0.05-0.28) | <0.0001 | R, N |
| 0103-0601 | 19 (1.10) | 5 (0.28) | 0.26 (0.11-0.71) | 0.0037 | 1 (0.08) | 0.07 (0.02-0.55) | 0.0007 | R, N |
| 0501-0301 | 212 (11.86) | 55 (3.03) | 0.23 (0.17-0.32) | <0.0001 | 38 (2.92) | 0.22 (0.16-0.32) | <0.0001 | R, N |
| 0102/3-0603 | 111 (6.21) | 28 (1.54) | 0.24 (0.16-0.36) | <0.0001 | 20 (1.54) | 0.24 (0.15-0.39) | <0.0001 | R, N |
| 0102-0609 | 23 (1.29) | 8 (0.44) | 0.34 (0.16-0.78) | 0.0060 | 5 (0.38) | 0.30 (0.13-0.81) | 0.0091 | R, N |
| 0301/2-0302/4-DRB1-0403 | 31 (1.73) | 13 (0.72) | 0.41 (0.22-0.79) | 0.0055 | 9 (0.69) | 0.40 (0.20-0.85) | 0.0115 | R, N |
| 0201-0202 | 136 (7.61) | 90 (4.96) | 0.63 (0.48-0.84) | 0.0011 | 53 (4.08) | 0.52 (0.38-0.72) | <0.0001 | R, N |
| 0301/2-0301 | 128 (7.16) | 88 (4.85) | 0.66 (0.50-0.88) | 0.0035 | 63 (4.85) | 0.66 (0.49-0.90) | 0.0084 | R, N |
| 0101/2/3-0501 | 190 (10.63) | 150 (8.27) | 0.76 (0.61-0.95) | 0.0155 | 111 (8.54) | 0.79 (0.61-1.01) | 0.0534 | R, N |
| 0102-0502 | 26 (1.45) | 21 (1.16) | 0.79 (0.45-1.41) | 0.4331 | 14 (1.08) | 0.74 (0.39-1.43) | 0.3601 | R, N, S |
| 0401-0402 | 60 (3.36) | 57 (3.14) | 0.93 (0.64-1.35) | 0.7178 | 43 (3.31) | 0.99 (0.66-1.47) | 0.9415 | R, N, S |
| 0102-0604 | 56 (3.13) | 73 (4.02) | 1.30 (0.91-1.84) | 0.1496 | 44 (3.38) | 1.08 (0.73-1.62) | 0.6954 | R, N, S |
| 0301-0401 | 5 (0.28) | 4 (0.22) | 0.79 (0.23-2.80) | 0.7519 | 1 (0.08) | 0.27 (0.06-2.27) | 0.4111 | N, S |
| 0301/2-0302/4-no 04 | 5 (0.28) | 5 (0.28) | 0.99 (0.30-3.21) | 0.9818 | 5 (0.38) | 1.38 (0.42-4.50) | 0.6122 | N, S |
| 0302-0303 | 23 (1.29) | 35 (1.93) | 1.51 (0.89-2.53) | 0.1252 | 27 (2.08) | 1.63 (0.93-2.83) | 0.0857 | N, S |
| 0501-0201 | 219 (12.25) | 536 (29.55) | 3.00 (2.52-3.57) | <0.0001 | 392 (30.15) | 3.09 (2.57-3.71) | <0.0001 | S |
| 0301/2-0302/4-not DRB1-0403 | 160 (8.95) | 594 (32.75) | 4.95 (4.09-5.97) | <0.0001 | 444 (34.15) | 5.28 (4.31-6.42) | <0.0001 | S |
| 0302-0202 | 3 (0.17) | 19 (1.05) | 6.30 (1.77-17.32) | 0.0007 | 13 (1.00) | 6.01 (1.35-17.37) | 0.0015 | S |
| Others | 12 (0.67) | 6 (0.33) | 0.49 (0.20-1.32) | 0.1475 | 4 (0.31) | 0.46 (0.17-1.45) | 0.1649 | |

Others = 0102-0504, 0301-0402, 0501-0302, 0501-0304

TABLE 2B

Caucasian

| | | All T1D | | | <22 T1D | | | S = Susceptible; N = Neutral; R = Resistant | |
|---|---|---|---|---|---|---|---|---|---|
| Haplotype | Caucasian population frequency (n = 1586) n (%) | Caucasian all T1D (n = 1706) n (%) | Odds Ratio (95% CI) | p value (alpha = 0.0023) | Caucasian <22 T1D (n = 1228) n (%) | Odds Ratio (95% CI) | p value (a = 0.0023) | haplotype risk for computer strategies | DEW-it strategy |
| 0103/4-0503 | 44 (2.77) | 1 (0.06) | 0.02 (0.01-0.16) | <0.0001 | 1 (0.08) | 0.03 (0.01-0.22) | 0.0001 | R | R |
| 0102/3/4-0602 | 223 (14.06) | 14 (0.82) | 0.05 (0.03-0.09) | <0.0001 | 6 (0.49) | 0.03 (0.01-0.07) | <0.0001 | R | R |
| 0601-0301 | 5 (0.32) | 0 (0.00) | 0 (0.004-1.52) | 0.0259 | 0 (0.00) | 0 (0.006-2.12) | 0.0725 | R | R |
| 0201-0303 | 57 (3.59) | 10 (0.59) | 0.16 (0.08-0.32) | <0.0001 | 5 (0.41) | 0.11 (0.05-0.29) | <0.0001 | N, R | R |
| 0103-0601 | 11 (0.69) | 2 (0.12) | 0.17 (0.05-0.79) | 0.0084 | 1 (0.08) | 0.12 (0.03-0.92) | 0.0135 | N, R | R |
| 0501-0301 | 190 (11.98) | 52 (3.05) | 0.23 (0.17-0.32) | <0.0001 | 35 (2.85) | 0.22 (0.15-0.31) | <0.0001 | N, R | R |
| 0102/3-0603 | 99 (6.24) | 26 (1.52) | 0.23 (0.15-0.36) | <0.0001 | 20 (1.63) | 0.25 (0.16-0.41) | <0.0001 | N, R | R |
| 0102-0609 | 20 (1.26) | 6 (0.35) | 0.28 (0.12-0.71) | 0.0032 | 4 (0.33) | 0.26 (0.10-0.78) | 0.0075 | N, R | N |
| 0301/2-0302/4-DRB1-0403 | 23 (1.45) | 13 (0.76) | 0.52 (0.27-1.04) | 0.0578 | 9 (0.73) | 0.50 (0.24-1.11) | 0.0751 | N, R | R |
| 0201-0202 | 114 (7.19) | 85 (4.98) | 0.68 (0.51-0.91) | 0.0080 | 51 (4.15) | 0.56 (0.40-0.79) | 0.0007 | N, R | R |
| 0301/2-0301 | 120 (7.57) | 83 (4.87) | 0.62 (0.47-0.83) | 0.0013 | 60 (4.89) | 0.63 (0.46-0.87) | 0.0040 | N, R | R |

TABLE 2B-continued

| | Caucasian | | | | | | | S = Susceptible; N = Neutral; R = Resistant | |
|---|---|---|---|---|---|---|---|---|---|
| | Caucasian | All T1D | | | <22 T1D | | | | |
| | Caucasian population frequency (n = 1586) n (%) | Caucasian all T1D (n = 1706) n (%) | Odds Ratio (95% CI) | p value (alpha = 0.0023) | Caucasian <22 T1D (n = 1228) n (%) | Odds Ratio (95% CI) | p value (a = 0.0023) | haplotype risk for computer strategies | DEW - it strategy |
| 0101/2/3-0501 | 170 (8.15) | 139 (8.15) | 0.74 (0.58-0.94) | 0.0115 | 101 (8.22) | 0.75 (0.58-0.97) | 0.0261 | S, N, R | N |
| 0102-0502 | 20 (1.26) | 14 (0.82) | 0.65 (0.33-1.29) | 0.2117 | 11 (0.90) | 0.71 (0.35-1.49) | 0.3572 | S, N, R | N |
| 0401-0402 | 54 (3.41) | 54 (3.17) | 0.93 (0.63-1.36) | 0.6999 | 40 (3.26) | 0.96 (0.63-1.45) | 0.8291 | S, N, R | S |
| 0102-0604 | 52 (3.28) | 69 (4.05) | 1.24 (0.86-1.79) | 0.2433 | 41 (3.34) | 1.02 (0.68-1.55) | 0.9296 | S, N, R | N |
| 0301-0401 | 1 (0.06) | 0 (0.00) | 0.00 (0.01-7.60) | 0.4818 | 0 (0.00) | 0.00 (0.02-10.57) | 1.0000 | S, N | S |
| 0301/2-0302/4-no 04 | 5 (0.32) | 5 (0.29) | 0.93 (0.28-3.04) | 1.0000 | 5 (0.41) | 1.29 (0.40-4.22) | 0.6845 | S, N | S |
| 0302-0303 | 19 (1.20) | 26 (1.52) | 1.28 (0.70-2.28) | 0.4208 | 21 (1.71) | 1.43 (0.77-2.65) | 0.2551 | S, N | S |
| 0501-0201 | 194 (12.23) | 516 (30.25) | 3.11 (2.59-3.73) | <0.0001 | 377 (30.70) | 3.19 (2.61-3.85) | <0.0001 | S | S |
| 0301/2-0302/4-not DRB1-0403 | 155 (9.77) | 570 (33.41) | 4.63 (3.81-5.61) | <0.0001 | 426 (34.69) | 4.90 (3.99-5.99) | <0.0001 | S | S |
| 0302-0202 | 3 (0.19) | 16 (0.94) | 5.00 (1.39-14.02) | 0.0046 | 11 (0.09) | 4.77 (1.29-14.17) | 0.0082 | S | S |
| Others | 7 (0.44) | 5 (0.29) | 0.66 (0.23-2.05) | 0.4806 | 3 (0.24) | 0.55 (0.17-2.14) | 0.3836 | N | N |

Others = 0102-0504, 0301-0402, 0501-0302, 0501-0304

Haplotypes were assigned into risk categories using a simple manual method and a computer program. For both methods, the top two haplotypes in Table 2 were seldom found in cases of T1D and were fixed as R, while the bottom two haplotypes, which clearly conferred disease risk, were fixed as S, and the rare haplotype group was fixed as N based on insufficient data. The seventeen remaining intermediate risk haplotypes were allowed to wobble between different risk categories. For the manual assignment, these intermediate haplotypes were kept in order of relative risk. A variable number of them (from three to seventeen) was then assigned as N in a contiguous block. The contiguous N block was shifted up and down within the seventeen haplotypes, with all haplotypes above the block assigned R and all below the block assigned S. This resulted in 121 different "manual" strategies.

A computer program was developed that allowed every possible assignment of haplotypes into risk categories to be exhaustively evaluated. For the computer-generated strategies, the seventeen remaining intermediate risk haplotype groups were allowed to be assigned into one of the three risk categories. Each arrangement of haplotypes constituted a hypothetical risk-evaluation strategy. Every possible unique hypothetical risk strategy was iteratively tested for sensitivity (proportion of T1D cases detected) and specificity (proportion of healthy controls excluded from autoantibody follow-up testing) on the WA state data. A non-parametric ROC (receiver operating characteristic) curve was plotted using sensitivity (percentage of T1D cases that would be detected by autoantibody screening) versus 1-specificity (percentage of population screened genetically who would receive follow-up autoantibody screening).

FIG. 1 shows the results of sensitivity versus specificity for the computer strategy. Due to the discrete nature of HLA haplotypes and genotypes, the curve is not continuous.

Many strategies resulted in the same specificity but differed in their sensitivity—only the set of best strategies is presented (i.e. the highest sensitivity strategy for each given specificity, the highest specificity for each given sensitivity).

As can be seen from FIG. 1, the best strategies had a specificity between 4-30%. As expected, higher sensitivities were associated with lower specificities.

Figure 2:
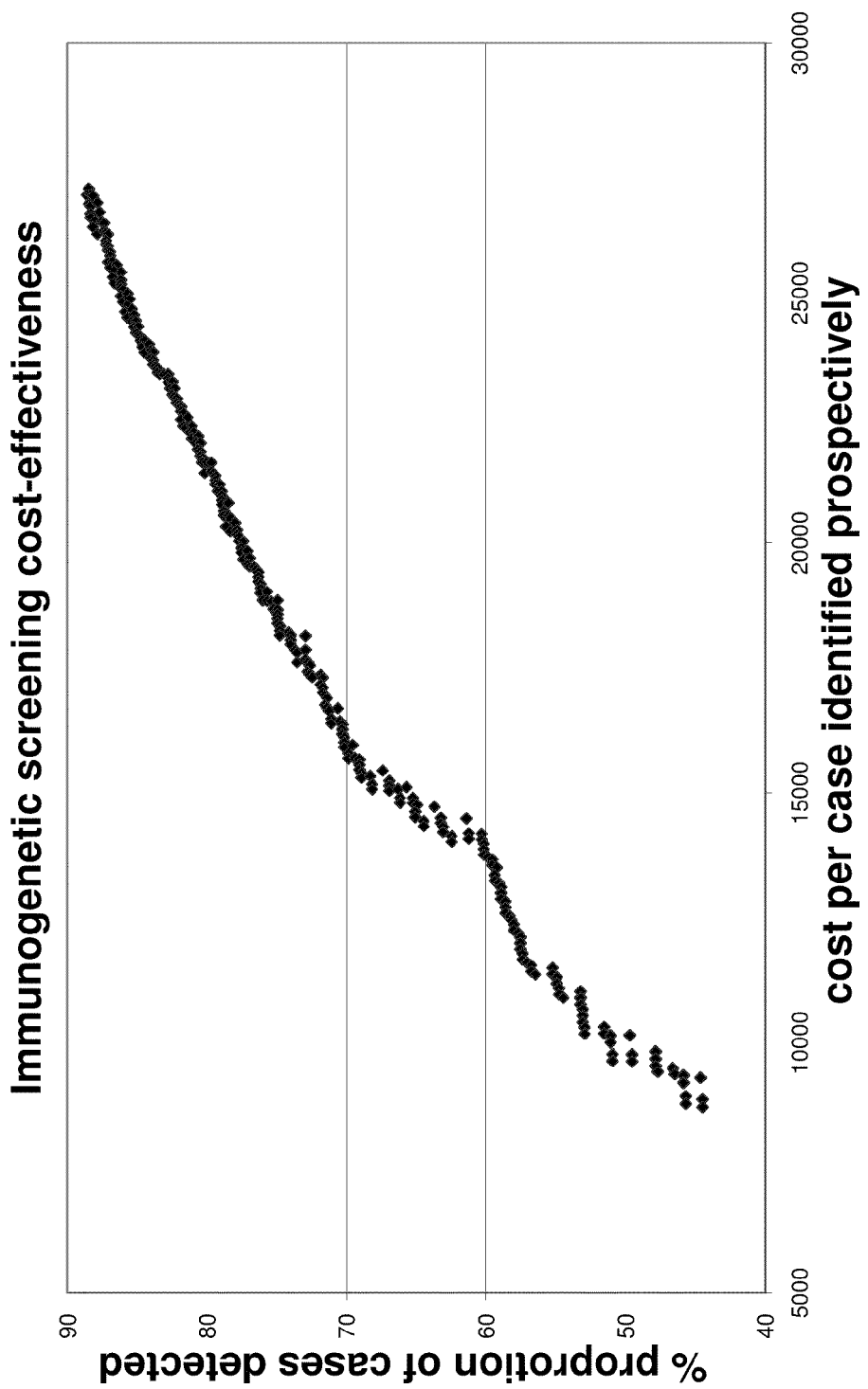
FIG. 2 shows the cost-effectiveness of immunogenetic screening for T1D.

FIG. 2 is a graph of the cost per identified T1D case versus the prediction strategy sensitivity. From this graph, it can be seen that identification of 60-70% of T1D offers the best cost-effectiveness. Based on these cost considerations, haplotype screening strategies which lead to detection of 60-80% of future T1D cases by performing follow-up autoantibody testing on 10-20% of the screened population were determined to be of most interest.

Figure 3:
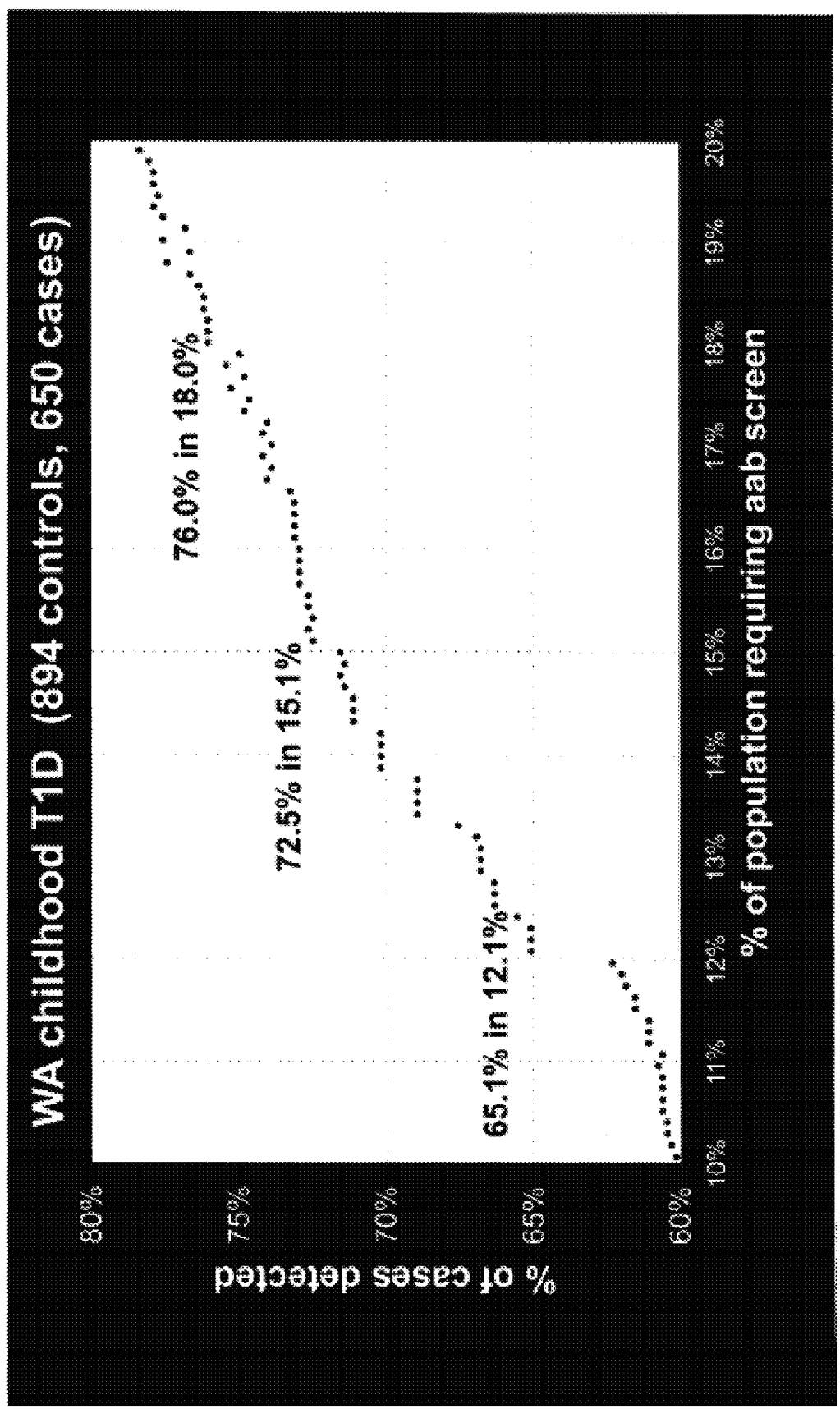
FIG. 3 shows specificity versus sensitivity for a subset of the strategies of FIG. 1, including for three strategies of most interest.

FIG. 3 presents a subset of the strategies shown in FIG. 1, namely strategies that achieved 60-80% of T1D cases detected within 10-20% of the population. Three of the most informative strategies are marked. These represent detection of 65.1% of future T1D cases by follow-up testing of 11.8% of the pediatric population for autoantibodies, 72.5% of cases by follow-up testing of 15.6% of children, and 76.0% of cases by follow-up testing of 17.9% of children. The attractiveness of higher sensitivity must be weighed against lower specificity, in this case the greater expense and invasiveness of following a larger proportion of the general pediatric population for periodic autoantibody testing during childhood.

EXAMPLE 2

The presence of one or more specific alleles in a biological sample is identified as follows. The method comprises PCR amplification followed by oligonucleotide probe hybridization using a commercially available time-resolved fluorescence (TRF) assay.

DNA amplification by polymerase chain reaction (PCR) was performed using either dried blood spot ⅛ inch punches or genomic DNA purified from whole frozen blood (QiaAmp, Qiagen) as template. DBS were amplified in 96-well microtiter plates by the PCR procedure. The reaction mixture was: DBS, 1×PCR buffer (16 mM $(NH_4)_2SO_4$, 67 mM Tris-HCL (pH 8.8 at 25° C.), 0.01% Tween 20), 5.5% glycerol, 2.0 mM $MgCl_2$, 0.2 mM each of dATP, dCTP, dTTP and dGTP, 0.35 pM DQA1 primers and 0.25 pM DQB1 primer, 3.5 unit DNA polymerase (Bioline, MA, USA) and DNAase free molecular grade water for a total volume of 100 ul. PCR primers for DQA1 were Biotin-5'-TAT GGT GTA AAC TTG TAC CAG T-3'(sense; SEQ ID NO: 1), 5'-GGT AGC AGC GGT AGA GTT G-3'(antisense; SEQ ID NO: 2). PCR primers for DQB1 were 5'-GCA TGT GCT ACT TCA CCA ACG-3'(sense; SEQ ID NO: 3), Biotin-5'-CCT TCT GGC TGT TCC AGT ACT-3'(antisense; SEQ ID NO: 4). PCR amplifications were performed on automated PCR thermal cycler (PTC-200, Peltier thermal cycler, MJ Research, New Jersey) with 34 cycles as follows: 10 minute at 95° C., followed by 34 cycles of 50 second at 95° C., 1 minute at 55° C., 1 minute at 72° C., then 5 minute at 72° C. A small portion of the amplified mixture was evaluated by 2% agarose gel electrophoresis to verify successful amplification.

For the Time-Resolved Fluorescence (TRF) assay, 10 ul of biotinylated PCR product was directly transferred to streptavidin-coated microtitration plates (Pierce), incubated with 50 ul of hybridization solution for 30 minutes at room temperature, and denatured with 20 mmol/L NaOH for 5 minutes at room temperature. The PCR products were then hybridized for 2 hours with a mixture of three allele sequence-specific probes (Delfia, Perkin-Elmer) that each carry a different lanthanide chelate (europium (Eu), samarium (Sm) or Terbium (Tb)). The probes were each used at a final concentration of 1.0 ng-1.5 ng/well). After incubation, stringent washes with wash solution (Delfia, Perkin Elmer) were performed at 45° C., and 200 ul of enhancement solution (Delfia, Perkin Elmer) was added to enhance the Eu and Sm fluorescence. Microtiter plates were counted on a Victor$^2$ fluorescence counter (Perkin-Elmer Wallac Oy, Turku, Finland) to measure the Eu and Sm TRF signals. Then 50 ul of enhancer solution (Delfia, Perkin Elmer) was added prior to measuring the Tb-fluorescence, also on a Victor$^2$ microtiterplate counter (Perkin-Elmer Wallac Oy). The details of the assay have been described previously (13). The lanthanide chelates probes, hybridization buffer, washing buffer, enhancement and enhancer were commercial reagents from PE-Wallac DELFIA system (Wallac OY, Turku, Finland). We modified the three allele specific probes combination of the multiplex assay to function accurately and cost-effectively for the specific research goal for the T1D general population screen, for example using a mixture of Eu-DQB1*05/06, Sm-DQB1*0301 and Tb-DQA1*0201. The DQB1*05/06 probe was designed by Drs. Hagopian and Peng as 5'-Eu-CAG GGG CGG CT-3' (SEQ ID NO: 5), and then manufactured to their specification including Eu chelate labeling, by Perkin-Elmer Wallac. An alternative probe also manufactured to specification including Eu chelate labeling by Perkin-Elmer Wallac, was the DQB1*0503/0601 probe: 5'-Eu-GGC GGC CTG ACG-3' (SEQ ID NO: 6). The Sm-DQB1*0301 and Tb-DQA1*0201 probes are available from Perkin-Elmer Wallac as catalog items. In some strategies from Table 1, two sets of probes were used in parallel assays on separate microtiter plates, with each set comprising up to three separate Lanthanide-labeled oligonucleotide probes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

SEQ ID NO: 1-6 are set out in the attached Sequence Listing. The codes for nucleotide sequences used in the attached Sequence Listing, including the symbol "n," conform to WIPO Standard ST.25 (1998), Appendix 2, Table 1.

REFERENCES

1. Barker J M, Goehrig S H, Barriga K, Hoffman M, Slover R, Eisenbarth G S, Norris J M, Klingensmith G J, Rewers M: Clinical characteristics of children diagnosed with type 1 diabetes through intensive screening and follow-up. *Diabetes Care* 27:1399-1404, 2004
2. Dahlquist G, Blom L, Holmgren G, Hägglöf B, Larsson Y, Sterky G, Wall S: The epidemiology of diabetes in Swedish children 0-14 years old: a six-year prospective study. *Diabetologia* 28:802-808, 1985
3. Tuomilehto J, Lounamaa R, Tuomilehto-Wolf E, Reunanen A, Virtala E, Kaprio E A, Akerblom H K: Epidemiology of childhood diabetes mellitus in Finland—background of a nationwide study of type 1 (insulin-dependent) diabetes mellitus. The Childhood Diabetes in Finland (DiMe) Study Group. *Diabetologia* 35:70-76, 1992
4. Pociot F, Norgaard K, Hobolth N, Andersen O, Nerup J: A nationwide population-based study of the familial aggregation of type 1 (insulin-dependent) diabetes mellitus in Denmark. Danish Study Group of Diabetes in Childhood. *Diabetologia* 36:870-875, 1993
5. Wagener D K, Kuller L H, Orchard T J, LaPorte R E, Rabin B, Drash A L: Pittsburgh diabetes mellitus study. II. Secondary attack rates in families with insulin-dependent diabetes mellitus. *AM. J. Epidemiol.* 115:868-878, 1982
6. Hagopian W, Sanjeevi C, Kockum I, Landin-Olsson M, Karlsen A, Sundkvist G, Dahlquist G, Palmer J, Lernmark Å: Glutamate decarboxylase-, insulin- and islet cell-antibodies and HLA typing to detect diabetes in a general population-based study of Swedish children. *J Clin Invest* 95:1505-1511, 1995
7. Rewers M, Bugawan T L, Norris J M, Blair A, Beaty B, Hoffman M, McDuffie R S, Jr., Hamman R F, Klingensmith G, Eisenbarth G S, Erlich H A: Newborn screening for HLA markers associated with IDDM: diabetes autoimmunity study in the young (DAISY). *Diabetologia* 39:807-812, 1996
8. Morales A, She J, Schatz D: Prediction and prevention of type 1 diabetes. *Curr Diab Rep* 1:28-32, 2001
9. Bennett-Johnson S, Baughcum A, Carmichael S, She J, Schatz D: Maternal anxiety associated with newborn genetic screening for type 1 diabetes. *Diabetes Care* 27:392-397, 2004
10. Hahl J, Simell T, Ilonen J, Knip M, Simell O: Costs of predicting IDDM. *Diabetologia* 41:79-85, 1998
11. Wion E, Brantley M, Stevens J, Gallinger S, Peng H, Glass M, Hagopian W: Population-wide infant screening for HLA-based type 1 diabetes risk via dried blood spots from the public health infrastructure. *Ann N Y Acad Sci* 1005: 400-403, 2003
12. Kiviniemi M, Hermann R, Nurmi J, Ziegler A G, Knip M, Simell O, Veijola R, Lovgren T, Ilonen J: A high-throughput population screening system for the estimation of genetic risk for type 1 diabetes: an application for the 12. TEDDY (the Environmental Determinants of Diabetes in the Young) study. *Diabetes Technol Ther* 9:460-472, 2007
13. Sjoroos M, Iitia A, Ilonen J, Reijonen H, Lovgren T: Triple-label hybridization assay for type-I diabetes-related HLA alleles. *Biotechniques* 18:870-877, 1995
14. Nikiforov T T, Rendle R B, Goelet P, Rogers Y H, Kotewicz M L, Anderson S, Trainor G L, Knapp M R: Genetic Bit Analysis: a solid phase method for typing single nucleotide polymorphisms. *Nucleic Acids Res* 22:4167-4175, 1994
15. Chen J, Iannone M A, Li M S, Taylor J D, Rivers P, Nelsen A J, Slentz-Kesler K A, Roses A, Weiner M P: A microsphere-based assay for multiplexed single nucleotide polymorphism analysis using single base chain extension. *Genome Res* 10:549-557, 2000
16. Han M, Tan Y Q, Zhang Y, Tsai J, Vorhaben R, Moraes J R, Moraes M E, Stastny P: Multiplex single nucleotide extension: a robust and high throughput method for HLA-A locus typing. *Hum Immunol* 64:1111-1122, 2003
17. LaGasse J, Brantley M, Leech N, Rowe R, Monks S, Palmer J, Nepom G, McCulloch D, Hagopian W: Successful prospective prediction of type 1 diabetes in schoolchildren through multiple defined autoantibodies: an 8-year follow-up of the Washington State Diabetes Prediction Study. *Diabetes Care* 25:505-511, 2002
18. Berger B, Stenstrom G, Sundkvist G: Random C-peptide in the classification of diabetes. *Scand J Clin Lab Invest* 60:687-693, 2000
19. Woo W, LaGasse J, Zhou Z, Patel R, Palmer J P, Campus H, Hagopian W A: A novel high-throughput method for accurate, rapid, and economical measurement of multiple type 1 diabetes autoantibodies. *J. Imm. Methods* 244:91-103, 2000
20. Erlich H, Bugawan T, Begovich A B, Scharf S, Griffith R, Saiki R, Higuchi R, Walsh P S: HLA-DR, DQ and DP typing using PCR amplification and immobilized probes. *Eur J Immunogenet* 18:33-55, 1991
21. Tsuji K, Aizawa M, Sasazuki T: HLA 1991. New York, Oxford University Press, 1992
22. Mori M, Beatty P, Graves M, Boucher K, Milford E: HLA gene and haplotype frequencies in the North American population: the National Marrow Donor Program Donor Registry. *Transplantation* 64:1017-1027, 1997
23. Kimura A, Sasazuki T: 11th International Histocompatiblity Workshop protocols for DNA-typing. In *HLA 1991: 11th International Histocompatiblity Workshop* Tsuji K, Aizawa M, Sasazuki T, Eds. Oxford, UK, Oxford University Press, 1992, p. 397-419
24. Ju L, Gu X, Bardie R, Krishnamoorthy R, Charron D: A simple nonradioactive method of DNA typing for subsets of HLA-DR4: prevalence data on HLA-DR4 subsets in three diabetic population groups. *Hum Immunol* 31:251-258, 1991
25. Klitz W, Maiers M, Spellman S, Baxter-Lowe L, Schmeckpeper B, Williams T, Femandez-Vina M: New HLA haplotype frequency reference standards: high-resolution and large sample typing of HLA DR-DQ haplotypes in a sample of European Americans. *Tissue Antigens* 62:296-307, 2003
26. Pugliese A, Gianani R, Moromisato R, Awdeh Z L, Alper C A, Erlich H A, Jackson R A, Eisenbarth G S: HLA-DQB1*0602 is associated with dominant protection from diabetes even among islet cell antibody-positive first-degree relatives of patients with IDDM. *Diabetes* 44:608-613, 1995
27. Roep B O, R S, W V, G J B, G M S, R R d: HLA-DRB1*0403 is associated with dominant protection against IDDM in the general Dutch population and subjects with high-risk DQA1*0301-DQB1*0302/DQA1*0501-DQB1*0201 genotype. *Tissue Antigens* 54:88-90, 1999
28. Thorsby E, Ronningen K: Particular HLA-DQ molecules play a dominant role in determining susceptibility or resistance to type 1 (insulin-dependent) diabetes mellitus. *Diabetologia* 36:371-377, 1993
29. Pugliese A: Unraveling the genetics of insulin-dependent diabetes: the search must go on. *Diabetes Reviews* 7:39-54, 1999

We claim:

1. A method for identifying an individual not in need of follow-up testing for T1D, comprising:
   (a) amplifying DNA in a nucleic acid-containing sample obtained from the individual using oligonucleotide primers specific for exons two of HLA DQB1 and DQA1 loci to provide amplified DNA;
   (b) simultaneously contacting the amplified DNA with a set of oligonucleotide probes, the set of oligonucleotide probes consisting of: a first oligonucleotide probe specific for DQA1*02, a second oligonucleotide probe specific for DQB1*0301, a third oligonucleotide probe specific for DQB1*0503 and DQB1*0601, a fourth oligonucleotide probe specific for DQB1*0602 and DQB1*0603, a fifth oligonucleotide probe specific for DQB1*0302 and a sixth oligonucleotide probe specific for DQB1*02 for a period of time sufficient for the oligonucleotide probes to hybridize to the amplified DNA; and
   (c) identifying that the individual is not in need of testing for T1D by the presence of DNA that binds to any one of the first, second, third and fourth oligonucleotide probes or the absence of DNA that binds to at least one of the fifth and sixth oligonucleotide probes.

2. The method of claim 1, wherein each of the oligonucleotide probes is labelled with a detection reagent.

3. The method of claim 1, wherein the oligonucleotide probes are immobilized on a solid substrate.

4. The method of claim 1, wherein the nucleic acid-containing sample is selected from the group consisting of: blood, urine, saliva and sera.

5. The method of claim 2, wherein the detection reagent is selected from the group consisting of: europium, samarium and terbium.

6. The method of claim 1, wherein the third oligonucleotide probe consists of the sequence of SEQ ID NO: 6.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Made in a lab

<400> SEQUENCE: 1
tatggtgtaa acttgtacca gt                                              22

<210> SEQ ID NO 2
<211> LENGTH: 19
<212> TYPE: DNA
<213> ORGANISM: Artificial Sequence
<220> FEATURE:
<223> OTHER INFORMATION: Made in a lab

<400> SEQUENCE: 2
ggtagcagcg gtagagttg                                                  19

<210> SEQ ID NO 3
```

```
<211> LENGTH: 21
<212> TYPE: DNA
<213> ORGANISM: Artificial Sequence
<220> FEATURE:
<223> OTHER INFORMATION: Made in a lab

<400> SEQUENCE: 3
gcatgtgcta cttcaccaac g                                          21

<210> SEQ ID NO 4
<211> LENGTH: 21
<212> TYPE: DNA
<213> ORGANISM: Artificial Sequence
<220> FEATURE:
<223> OTHER INFORMATION: Made in a lab

<400> SEQUENCE: 4
ccttctggct gttccagtac t                                          21

<210> SEQ ID NO 5
<211> LENGTH: 11
<212> TYPE: DNA
<213> ORGANISM: Artificial Sequence
<220> FEATURE:
<223> OTHER INFORMATION: Made in a lab

<400> SEQUENCE: 5 cagggggcggc t                                                    11

<210> SEQ ID NO 6
<211> LENGTH: 12
<212> TYPE: DNA
<213> ORGANISM: Artificial Sequence
<220> FEATURE:
<223> OTHER INFORMATION: Made in a lab

<400> SEQUENCE: 6
ggcggcctga cg                                                    12
```